United States Patent [19]

Kollmeyer

[11] 4,183,857

[45] Jan. 15, 1980

[54] 3-BENZYL-3-AZABICYCLO(3.1.0)HEXANE-2,4-DIONE

[75] Inventor: Willy D. Kollmeyer, Modesto, Calif.

[73] Assignee: Shell Oil Company, Houston, Tex.

[21] Appl. No.: 922,407

[22] Filed: Jul. 6, 1978

[51] Int. Cl.² ............................................ C07D 209/52
[52] U.S. Cl. .......................... 260/326.5 B; 260/326.87
[58] Field of Search ...................... 260/326.5 B, 326.87

[56] References Cited

U.S. PATENT DOCUMENTS

| | | | |
|---|---|---|---|
| 3,418,336 | 12/1968 | Grogan et al. | 260/326.5 FM |
| 3,654,305 | 4/1972 | German | 260/326.5 FM |
| 3,745,170 | 7/1973 | Fujinam et al. | 260/326.5 FM |

OTHER PUBLICATIONS

Leonard M. Rice, J. Org. Chem. vol. 24, 1520–1523 (1959).
Wendish & Naegle, Org. Mag. Res. Spect. 2, 619–624 (1970).

*Primary Examiner*—Jose Tovar

[57] ABSTRACT

3-Azabicyclo(3.1.0)hexane, a precursor for preparing 3-azabicyclo(3.1.0)hexane-2-carboxylic acid, a plant gametocide, is prepared by (a) treating cis-1,2-cyclopropanedicarboxylic acid with benzylamine, to form 3-(benzyl)-3-azabicyclo(3.1.0)hexane-2,4-dione, (b) selectively reducing the dione to 3-(benzyl)-3-azabicyclo(3.1.0)hexane, and (c) hydrogenolysis of that compound to 3-azabicyclo(3.1.0)hexane.

2 Claims, No Drawings

3-BENZYL-3-AZABICYCLO(3.1.0)HEXANE-2,4-DIONE

BACKGROUND

3-Azabicyclo(3.1.0)hexane-2-carboxylic acid has been found to be an effective plant male gametocide: U.S. Pat. No. 4,047,930 (the compound is designated therein as 2-carboxy-3,4-methanopyrrolidine). The compound exists in the forms of two geometric (i.e., cis, trans) isomers. Each of these isomeric forms exists in the forms of optical isomers. The racemic mixtures of both of the geometric isomer forms are active as plant male gametocides. The naturally occurring, L, cis isomer is active as a plant male gametocide; the relative activities of each of the other optical isomer forms have not been determined. The L, cis isomer occurs naturally in the seeds of the American horse chestnut, *Aesculus parviflora*.

3-Azabicyclo(3.1.0)hexane-2-carboxylic acid now can be prepared synthetically by the following route:

(1) 1,2-cyclopropanedicarboxylic acid is treated with benzylamine to form 3-(benzyl)-3-azabicyclo(3.1.0)hexane-2,4-dione (I).

(2) I is selectively reduced to 3-(benzyl)-3-azabicyclo(3.1.0)hexane (II).

(3) II is catalytically hydrogenated to form 3-azabicyclo(3.1.0)hexane (III).

(4) III is chlorinated to give 3-chloro-3-azabicyclo(3.1.0)hexane (IV).

(5) A solution of IV is treated with a strong inorganic base and a lower alkanol, and solids are removed from the resulting reaction mixture, to give a solution of 3-azabicyclo(3.1.0)hex-2-ene (V).

(6) The solution of V is treated with an alkali metal bisulfite to form the 2-bisulfite adduct (VI) of 3-azabicyclo(3.1.0)hex-2-ene.

(7) The reaction mixture containing VI is treated with an alkali metal cyanide to form 3-azabicyclo(3.1.0)hexane-2-carbonitrile (VII).

(8) VII is treated with barium hydroxide to form the barium salt of 3-azabicyclo(3.1.0)hexane-2-carboxylic acid, which is treated with sulfuric acid to give a mixture of (±-trans and ±-cis)-3-azabicyclo(3.1.0)hexane-2-carboxylic acid, from which the two racemic mixtures can be isolated, if desired.

DESCRIPTION OF THE INVENTION

This invention is the above-described method for preparing 3-azabicyclo(3.1.0)cyclohexane—i.e., III, above.

The precursor cis-1,2-cyclopropanedicarboxylic acid can be prepared by conventional treatment of a diester thereof, which can be prepared as described in McCoy, Journal of the American Chemical Society, volume 80, pages 6568–6572 (1958). Preparation of the acid in a particular instance is described in Example 1, hereinafter.

According to the method of the invention, the acid is treated with an equimolar amount of benzylamine, at least initially in the presence of water, as solvent, at a moderately elevated temperature, for example, at a temperature of from about 150° C. to about 200° C. for sufficient time to ensure completion of the desired reaction—usually about 2–3 hours are required. One convenient technique for conducting the treatment is described in Example 2, hereinafter. The product can be recovered from the final reaction miture by removing the water (this is conveniently accomplished by distilling off the water during the course of the treatment), and pouring the crude product (ordinarily an oil) into a suitable liquid medium (such as isopropyl alcohol) in which the desired product is at most only sparingly soluble, but which is a solvent for any unreacted material and any by-products.

The 3-(benzyl)-3-azabicyclo(3.1.0)hexane-2,4-dione thus produced is treated, in a solvent, with a stoichiometric excess of an aluminum hydride reducing agent. Although as little as a forty percent excess is satisfactory, it is preferred to use from about two to about six moles of the reducing agent per mole of the dione. Ethers are suitable solvents. The hydrides ordinarily are marketed as solutions or dispersions in liquid hydrocarbons. Such products can be used directly, the hydrocarbon not interfering with the desired reaction, or the hydrocarbon may be removed. The treatment is best effected by mixing the reactants at a low temperature—for example, about 0° C. to about 15° C.— then heating the stirred mixture to a moderately elevated temperature, for example 50° C. to 75° C. The resulting miture then is treated with water or a water solution of an alkali metal base to destroy the excess reducing agent, and is filtered to remove inorganic salts and stripped of solvent to yield the crude desired product, from which the pure product can be isolated by conventional techniques.

Hydrogenolysis of the 3-(benzyl)-3-azabicyclo(3.1.0)hexane thus produced to 3-azabicyclo(3.1.0)hexane is effected by catalytic hydrogenation, using a palladium catalyst. The technique for conducting the hydrogenation is conventional, and is illustrated in Example 4. Thus, the hydrogenation is conveniently conducted by treating the benzyl compound under mild conditions— that is, treating it with hydrogen, under pressure, in the presence of a palladium-on-charcoal catalyst, and in a solvent, at about room temperature, or somewhat above, for a time sufficient to effect the hydrogenolysis. Suitable hydrogen pressures are from about 35 to about 100 pounds per square inch gauge. Suitable solvents are the lower alkanols, particularly ethanol. The reaction may be essentially complete in as little as 10–12 hours, or may require several days.

There appears to be a tendency for the azabicyclo(3.1.0)hexane to co-distill with the solvent. Recovery of the azabicyclo(3.1.0) hexane is facilitated by converting it to its hydrochloride salt, which is nonvolatile. The free compound (3-azabicyclo(3.1.0)hexane) can be prepared from the salt by known, conventional procedures.

The following examples illustrate conduct of the process of the invention in a particular instance. In these examples, the identities of the starting material, the intermediates and the product, all were confirmed by appropriate chemical and spectral analyses.

EXAMPLE 1—Preparation of (cis,trans)-1,2-cyclopropanecarboxylic Acid (1)

With exclusion of moisture, a stirred mixture of 43.3 g (1.01 mol) of 56% sodium hydride-mineral oil dispersion in 200 ml of toluene was treated with 10–20 ml of a blend of 100.1 ml g (1 mol) ethyl acrylate and 122.6 g (1 mol) ethyl chloroacetate followed by several drops of ethanol. After an induction period of about 1 hr, steady gas and heat evolution began. Then the remaining mixed ester reagent was carefully added dropwise with ice-bath cooling so as to maintain a reaction temperature of 30°–38° C. After addition was completed (4 hrs), the mixture was cooled, washed with water, and dried (MgSO$_4$). Distillation gave diethyl (cis,trans)-1,2-cyclopropanedicarboxylate, (1A), as a colorless liquid, bp: 78°–89° C. (0.7 Torr.). (Literature value: 50°–90° C. (1 Torr.)).

Saponification of 190.1 g (1.02 mol) of 1A was achieved with 116.0 g (2.90 mol) of sodium hydroxide in 780 ml water at reflux for 5 hrs. After removal of ethanol with a rotary evaporator, the remaining solution was acidified with a slight excess of 12 N hydrochloric acid (268 ml, 3.2 mol). The resulting mixture was stripped to dryness. The solid residue was extracted with hot ethyl acetate (3×500 ml). Evaporation of solvent from the dried (MgSO$_4$) extracts gave 1, mp: 108°–128° C. (with gas evolution).

EXAMPLE 2—3-(Benzyl)-3-azabicyclo(3.1.0)hexane-2,4-dione (2)

A mixture of 128.1 g (0.984 mol) of 1, 100 ml of water, and 105.5 g (0.984 mol) of benzylamine was heated at 180° C., for 2 hrs, while water was allowed to distill out. The mixture then was cooled somewhat and the warm mixture was slowly poured into 1000 ml of isopropyl alcohol. The mixture was thoroughly chilled and filtered to give impure 2, mp: 90°–150° C. The major by-product appears to be a non-cyclic material formed from the trans-isomer of the acid. It is not readily separated from 2, but does not interfere in the subsequent reduction of 2, but forms a by-product from which 3 is readily separated (Example 3A).

EXAMPLE 3—3-(Benzyl)-3-azabicyclo(3.1.0) hexane (3)

A 142.3 g (0.707 mol) of 2 (product of Example 2) was added, in portions, to an ice-cooled and stirred suspension of 105.6 g (1.59 mol) of 57.2% lithium aluminum hydride/mineral oil dispersion in 2000 ml of tetrahydrofuran, the temperature of the mixture being maintained at or below 15° C. The mixture was cautiously brought to reflux temperature and refluxed for 4 hrs, and then was allowed to stand overnight at room temperature. Then, 200 ml of 50% sodium hydroxide solution, followed by 150 ml of water, were added over a 3-hr period. Celite was added and the mixture was filtered to remove inorganic salts. The filtrate was dried (MgSO$_4$), the solvent was evaporated, and the residue was distilled in the presence of several drops of Dow Corning Antifoam A, to give 3, bp: 73–74 (0.01 Torr.).

B 63.2 g (0.486 mol) of 1 was added in portions to 150 ml of thionyl chloride. The mixture was refluxed for 1 hour, then was stripped. The residue was distilled to give cis-1,2-cyclopropanedicarboxylic acid anhydride (3A) bp 134° C. (10 Torr.). 2.14 g (0.02 mol) of benzylamine was carefully added to 2.24 g (0.02 mol) of 3A (CAUTION: THE REACTION IS VERY EXOTHERMIC.) The mixture was heated at 180° C. for 2 hours. After cooling, the residue was recrystallized from isopropyl alcohol to give 3-(benzyl)-3-azabicyclo(3.1.0)hexane-2,4-dione, as white needles, mp 90°–91° C. (3B). A cooled (0°) solution of 305 ml (1.09 mol) of 70% sodium bis(2-methoxyethoxy)aluminum hydride in benzene diluted with 600 ml of ether was treated with 48.7 g (0.24 mole) of 3B. The mixture was stirred at 0° for ½ hr and refluxed for 3 hrs. After standing at room temperature overnight, excess metal hydride was destroyed by cautiously adding cold water. The mixture was filtered after addition of diatomaceous silica (Celite). The ether layer was removed and the aqueous layer was extracted with ether. The combined organic layers were dried (MgSO$_4$). Ether and 2-methoxyethanol were evaporated under reduced pressure to give 3, as an oil. Distillation gave 3, bp: 79°–80° C. (0.01 Torr.).

EXAMPLE 4—3-Azabicyclo(3.1.0)hexane (4)

Catalytic hydrogenation (2.05 g 10% palladium on charcoal) of 40.5 g (0.234 mol) of undistilled 3, procedure B, in 150 ml ethanol was carried out with a Paar apparatus (63 psig initially, room temperature) overnight. After filtration of catalyst, ethanol was fractionally distilled through a 40 cm Vigreux column. The product contained detectable (NMR) amounts of ethanol. Two fractions were collected: bp 104°–110° C. 7.78 g, purity 84% and bp 110°–114° C., 9.00 g, purity 94%. The relative amounts of 4 and impurity ethanol in these fractions were determined by NMR analysis.

EXAMPLE 5—3-Azabicyclo(3.1.0)hexane hydrochloride (5)

82.6 g (0.476 mol) of 3, procedure A, in 100 ml of absolute alcohol, was catalytically hydrogenated (4 g 10% palladium in charcoal) in a Parr apparatus for 5 days at room temperature, the pressure of the hydrogen being maintained at 63 psig. The catalyst was removed, 39.7 ml (0.476 mol) of concentrated hydrochloric acid was added and the solution was concentrated under reduced pressure. The last traces of water and ethanol were removed by azeotropic distillation with benzene to give 5, mp: 158°–161° C. An analytical sample, mp: 161°–163° C. (with gas evolution), was obtained by trituration of the above product with cold isopropyl alcohol.

EXAMPLE 6—(cis,trans)-3-Azabibyblo(3.1.0)hexane-2-carbonitrile (6)

A

A mixture of 11.8 g (0.0855 mol) of N-chlorosuccinimide, 4.16 g (0.05 mol) of 4 and 250 ml ether was stirred at room temperature for 2½ hrs. After filtration, the ethereal solution was washed with water (2×100 ml) and brine (1×50 ml). The dried (MgSO$_4$) filtrate was carefully concentrated to ca 40 ml total volume (40 cm Vigreux column). The remaining solution, containing 3-chloro-3-azabicyclo(3.1.0)hexane, was added dropwise (30 min) to a cooled (ice-bath) and stirred solution of 3.30 g (0.05 mol) of 85% potassium hydroxide in 25 ml of absolute ethanol. The white suspension was then stoppered and stirred at room temperature overnight (16 hrs). Filtration removed inorganic salts, which were washed with a little ether. The combined filtrate and ether washings, which contained the corresponding 3-azabicyclo(3.1.0)hex-2-ene, were treated with 5.20 g (0.05 mol) of sodium bisulfite in 25 ml water. After stirring vigorously for 1 hr at room temperature, the two-phase mixture containing the bisulfite adduct of 3-azabicyclo(3.1.0)hex-2-ene, was treated with 2.58 (0.05 mol) of 95% sodium cyanide as a solid for 1 hr at room temperature. The upper organic layer was decanted and the aqueous layer was further extracted with ether (2×100 ml, decantation). The combined organic layer and ether extracts were concentrated on the rotary evaporator (water aspirator pressure, 70° C.). The oily residue was diluted with 75 ml ether causing a small aqueous phase to separate. The resulting two-phase mixture was dried (MgSO$_4$) and the solvent was evaporated under reduced pressure to give 6, as a light yellow oil. An analytical sample of 6 was a colorless oil, bp: 62° C. (0.005 Torr.).

B 56.9 g (0.476 mol) of 5 was added to 150 ml of a saturated solution of potassium hydroxide in water. The separated oil was dissolved in 200 ml of ether, the solution was dried (MgSO$_4$), and 112.5 g (0.842 mol) of N-chlorosuccinimide in 800 ml of ether was added. The mixture was stirred for 3 hrs at room temperature, then filtered, washed with water and sodium chloride solution, dried (MgSO$_4$) and carefully concentrated to about 200 ml volume in a Vigreaux column. The resulting solution was added dropwise over a 30-minute period to a cooled (ice-bath) and stirred solution of 31.4 g (0.476 mol) of 85% potassium hydroxide in 200 ml of absolute ethanol. The resulting suspension was stirred at room temperature overnight, then filtered to remove inorganic salts. The filtrate was treated with 49.5 g (0.476 mol) of sodium bisulfite in 200 ml of water. After stirring for 75 minutes at room temperature, the two-phase mixture was treated with 24.6 g (0.476 mol) of 95% sodium cyanide. The mixture was stirred for 2 hours at room temperature, the organic phase was separated, and the aqueous phase was extracted with ether. The combined organic phase and extract was concentrated under reduced pressure. The residue was diluted with 200 ml of ether. A small aqueous phase separated. The two-phase mixture was dried (MgSO$_4$) and stripped of solvent. The residue was distilled to give 6, as a colorless liquid, bp: 58°-61° C. (0.01 Torr.).

C 12.6 g (0.15 mol) of sodium bicarbonate was added to a cooled (ice-bath) and stirred solution of 5.25% aqueous sodium hypochlorite, 212.7 g (0.15 mol). When most of the bicarbonate had dissolved, 12.0 g (0.10 mol) of 5 was added. The mixture was stirred (with cooling) for 1 hr and the resulting suspension was extracted with ether. The extract was dried (MgSO$_4$) and divided into two parts. One part was distilled in an attempt to isolate the 3-chloro-3-azabicyclo(3.1.0)hexane. However, the pot residue decomposed suddenly and vigorously when most of the ether had been distilled off, at 36° C. and ambient pressure. The other part of the extract was concentrated to about 25 ml, and added dropwise to a cooled (ice-bath) and stirred solution of 3.30 g (0.05 mol) of 85% potassium hydroxide in absolute ethanol. From this point on, the procedure followed that described in procedure B, above. 6 was obtained as a colorless oil, bp: 52°-54° C. (0.005 Torr.).

EXAMPLE

7—(±-cis)-3-azabicyclo(3.1.0)hexane-2-carboxylic acid hydrochloride (7) and the (±-trans)-isomer (8)

A mixture of 34.6 g (0.319 mol) of 6, 102.8 g (0.325 mol) of barium hydroxide octahydrate, and 500 ml of water was refluxed for 7 hrs. The mixture was cooled, and then carefully neutralized to pH 6 with 33.2 g (0.325 mol) of 96% sulfuric acid in 500 ml of water. Celite was added and the mixture was filtered. The solvent was evaporated and the residue was extracted with hot ethanol. The undissolved solid (7A) was an approximately 2/1 mixture of (±-trans)- and (±-cis)-3-azabicyclo(3.1.0)hexane-2-carboxylic acid. The solid obtained from evaporation of the solvent from the extract (7B) was an approximately 2.2/1 mixture of the (±-cis)- and (±-trans)-isomers.

7B was subjected to chromatography on a cation exchange resin, using 1.5 N hydrochloric acid as eluent, to give 7, as a solid, mp 226°-228° C. (with gas evolution), as the more mobile isomer. The less mobile isomer was 8, mp 202°-206° C. (with gas evolution).

I claim as my invention:
1. 3-Benzyl-3-azabicyclo(3.1.0)hexane-2,4-dione.
2. 3-Benzyl-3-azabicyclo(3.1.0)hexane.

* * * * *